United States Patent
Galvan Gonzalez

(10) Patent No.: US 9,801,916 B2
(45) Date of Patent: Oct. 31, 2017

(54) ORAL ANTISEPTIC COMPOSITION USEFUL FOR TREATING ORAL MUCOSITIS

(71) Applicant: Tomás Bernardo Galvan Gonzalez, Santiago (CL)

(72) Inventor: Tomás Bernardo Galvan Gonzalez, Santiago (CL)

(*) Notice: Subject to any disclaimer, the term of this patent is extended or adjusted under 35 U.S.C. 154(b) by 0 days.

(21) Appl. No.: 14/766,413

(22) PCT Filed: Feb. 7, 2013

(86) PCT No.: PCT/CL2013/000011
§ 371 (c)(1),
(2) Date: Aug. 6, 2015

(87) PCT Pub. No.: WO2014/121411
PCT Pub. Date: Aug. 14, 2014

(65) Prior Publication Data
US 2015/0374772 A1    Dec. 31, 2015

(51) Int. Cl.
| | |
|---|---|
| *A61K 36/28* | (2006.01) |
| *A61K 31/05* | (2006.01) |
| *A61K 31/055* | (2006.01) |
| *A61K 31/085* | (2006.01) |
| *A61K 31/125* | (2006.01) |
| *A61K 31/4425* | (2006.01) |
| *A61K 33/40* | (2006.01) |
| *A61K 9/00* | (2006.01) |
| *A61K 31/045* | (2006.01) |
| *A61K 45/06* | (2006.01) |
| *A61K 31/17* | (2006.01) |
| *A61K 31/175* | (2006.01) |
| *A61K 31/198* | (2006.01) |
| *A61K 31/351* | (2006.01) |
| *A61K 31/475* | (2006.01) |
| *A61K 31/513* | (2006.01) |
| *A61K 31/519* | (2006.01) |
| *A61K 31/675* | (2006.01) |
| *A61K 31/704* | (2006.01) |
| *A61K 31/7048* | (2006.01) |
| *A61K 31/7068* | (2006.01) |
| *A61K 31/7076* | (2006.01) |
| *A61K 33/24* | (2006.01) |
| *A61K 47/10* | (2017.01) |
| *A61K 47/26* | (2006.01) |

(52) U.S. Cl.
CPC .............. *A61K 36/28* (2013.01); *A61K 9/006* (2013.01); *A61K 31/045* (2013.01); *A61K 31/05* (2013.01); *A61K 31/055* (2013.01); *A61K 31/085* (2013.01); *A61K 31/125* (2013.01); *A61K 31/17* (2013.01); *A61K 31/175* (2013.01); *A61K 31/198* (2013.01); *A61K 31/351* (2013.01); *A61K 31/4425* (2013.01); *A61K 31/475* (2013.01); *A61K 31/513* (2013.01); *A61K 31/519* (2013.01); *A61K 31/675* (2013.01); *A61K 31/704* (2013.01); *A61K 31/7048* (2013.01); *A61K 31/7068* (2013.01); *A61K 31/7076* (2013.01); *A61K 33/24* (2013.01); *A61K 33/40* (2013.01); *A61K 45/06* (2013.01); *A61K 47/10* (2013.01); *A61K 47/26* (2013.01)

(58) Field of Classification Search
CPC ........ A61K 36/28; A61K 9/006; A61K 33/40; A61K 31/4425; A61K 31/055; A61K 31/085; A61K 31/05; A61K 31/125
See application file for complete search history.

(56) References Cited

U.S. PATENT DOCUMENTS

| | | | |
|---|---|---|---|
| 4,226,851 A | 10/1980 | Sompayrac | |
| 4,436,721 A | 3/1984 | Gaffer | |
| 5,104,644 A | 4/1992 | Douglas | |
| 6,348,187 B1 | 2/2002 | Pan et al. | |
| 6,509,028 B2 | 1/2003 | Williams et al. | |
| 2008/0247972 A1 | 10/2008 | Conceicao | |
| 2008/0299051 A1* | 12/2008 | Galvan | A61K 8/22 424/53 |
| 2009/0081134 A1 | 3/2009 | Pan et al. | |
| 2010/0035997 A1 | 2/2010 | Broadley et al. | |
| 2011/0244039 A1* | 10/2011 | Domb | A61K 9/006 424/464 |
| 2012/0148506 A1 | 6/2012 | Galvan Gonzalez | |

FOREIGN PATENT DOCUMENTS

| | | | | |
|---|---|---|---|---|
| CA | WO 2009043134 A1 * | 4/2009 | ............... | A61K 8/41 |
| CL | 44471 | 2/2009 | | |
| CL | WO 2011020206 A1 * | 2/2011 | ............... | A61K 8/21 |
| EP | 0161899 B1 | 8/1991 | | |
| EP | 1236466 A1 | 9/2002 | | |
| WO | 0000166 A2 | 1/2000 | | |

(Continued)

OTHER PUBLICATIONS

English Translation of WO 2011020206 A1. Translated from Google Patent on Aug. 30, 2016.*

(Continued)

*Primary Examiner* — Anoop Singh
*Assistant Examiner* — Doan Phan
(74) *Attorney, Agent, or Firm* — Hasse & Nesbitt LLC; Daniel F. Nesbitt

(57) ABSTRACT

Antiseptic pharmaceutical composition useful for the treatment of painful lesions in oral mucosa, ulcerative and inflammatory lesions of different origin and the treatment and/or prevention of oral mucositis and stomatitis.

4 Claims, No Drawings

(56) References Cited

FOREIGN PATENT DOCUMENTS

WO      2011020206 A1    2/2011
WO      2012078135 A1    6/2012

OTHER PUBLICATIONS

The Oral Cancer Foundation—"Mucositis." Retrieved Aug. 30, 2016. Retrieved from the internet <URL: http://www.oralcancerfoundation.org/complications/mucositis.php>.*

NHS choices—"Mucositis." Retrieved on Aug. 30, 2016. Retrieved from the internet <URL: http://www.nhs.uk/conditions/mucositis/Pages/Introduction.aspx>.*

International Search Report and Written Opinion dated Jul. 9, 2013, for corresponding International Application Serial No. PCT/CL2013/000011 (WO 2014/121411), filed Feb. 7, 2013 (18 pages).

International Search Report dated Jan. 17, 2011, for related International Application Serial No. PCT/CL2010/000030 (WO 2011/020206), filed Aug. 19, 2010 (3 pages).

* cited by examiner

ORAL ANTISEPTIC COMPOSITION USEFUL FOR TREATING ORAL MUCOSITIS

FIELD OF THE INVENTION

The present invention relates to pharmaceutical compositions, uses of such compositions and methods thereof, for the treatment of painful lesions of the oral mucosa, ulcerative lesions such as aphthous ulcers and the like, inflammatory lesions of different origin and, particularly, for the treatment and/or prevention of oral mucositis in anticancer therapy regimens. Particularly, the invention provides the use of an oral pharmaceutical composition for the treatment and/or prevention of oral mucosistis and stomatitis in anticancer therapy regimen. Additionally, the invention provides a method for the treatment of oral mucositis and stomatitis associated with anticancer therapies.

BACKGROUND OF THE INVENTION

Aphthous stomatitis is a disorder of the oral cavity that involves the formation of one or more ulcers, which may persist for several weeks leaving scars after healing. Such ulcers may reappear some years later, come back continuously with new lesions, even when previous lesions have not healed. The latter case is called recurrent aphthous stomatitis, and extreme cases may occur when the infection becomes chronic. Aphthous stomatitis affects both genders and, recently, attention has been drawn to the treatment and prevention of this pathology both in healthy patients and those with systemic diseases such as cancer or diabetes, since upon receiving their respective treatment therapies, it has been observed that in around 95% of them, stomatitis with some grade of severity will manifest, thus significantly impairing quality of life.

On the other hand, oral mucositis is an inflammatory disease that weakens oral mucosa, generally manifested as erythema and painful ulcerous lesions in the mouth and, in cases of oropharyngeal mucositis, also affecting the throat and esophagus. It is a common complication in anticancer therapies comprising radiotherapy and/or chemotherapy, and which may occur in up to 60% of average patients receiving such treatments.

Clinically, mucositis progresses through the following stages:

1. Atrophic changes associated with painful erythema of the mucosa, which respond to local anesthetics.
2. Painful ulceration with the formation of pseudomembrane and in cases of myelosuppressive treatment, generalized sepsis may occur, requiring antimicrobial therapy. Generally, the intensity of pain is such that it becomes necessary to apply parenteral analgesia with narcotics.
3. Spontaneous healing, usually occurring 2 to 3 weeks after completing the anticancer therapy.

Its incidence varies depending on the type of diagnosed tumor and the treatment thereof, the age of the patient, and oral health. Young patients present with higher incidence which may be due to a faster epithelial regeneration, and therefore susceptibility to cytotoxic drugs.

In the case of chemotherapeutic treatments, incidence is related to the choice of such agent. It has been observed that the agents carmustine (BICNU), chlorambucil (Leukeran), cisplatin (Platinol), cytarabine, doxorubicin (Adriamycin), fluorouracil (5-FU), methotrexate (Mexate) and plicamycin (Mithracin), have direct cytotoxic potential, and therefore they have a higher incidence of oral mucositis. The increasing use of aggressive management protocols is also associated with an increased incidence of oral mucositis.

In patients treated with radiotherapy, such as those diagnosed with brain and neck cancer, a daily radiation dose of around 200 cGy is usually given, during 5-7 consecutive weeks. Studies conducted show that almost all of patients will develop some degree of oral mucositis.

Two recent studies showed that in at least 94% to 96% of patients in the control group some degree of oral mucositis was developed (WHO assessment scale). Then, in 66% of patients from both studies, severe oral mucositis equivalent to grades 3 and 4 according to WHO scale was developed.

Currently, there is no universally accepted treatment protocol for the prevention and/or treatment of oral mucositis in patients receiving chemotherapy or radiotherapy, therefore, palliative care for this condition is standard procedure and may include:

Bland rinses, for example, saline solutions 0.9%, solutions of sodium bicarbonate or saline solutions 0.9% in combination with sodium bicarbonate;

Topical anesthetics, for example, viscous compositions, ointments, and sprays comprising lidocaine, sprays or gels comprising benzocaine, 0.5 or 1% dyclonine chloride, or solutions of diphenhydramine;

Mucosal coating agents, for example, suspensions of aluminum hydroxide, bismuth subsalicylate suspensions, products comprising film forming agents, cyanoacrylate Analgesics such as topical rinses of benzinamida chloride or opioid drugs given orally or intravenously (eg, bolus, continuous infusion), transdermally via patch or transmucosally;

Growth factors, such as keratinocyte growth factor (KGF), also called palifermin.

Oral mucositis, especially when severe (grade 3-4 according to WHO scale), results in a significant negative impact on the daily and general performance of the patient's mouth, including both communicating and feeding issues. For most patients receiving radiotherapy for brain and neck cancer, oral mucositis causes inability to feed through this via, due to pain of the mucosa and thus, the patient is instructed to feed through gastrostomy tubes or intravenously. Thus it has also been shown that patients with oral mucositis are significantly more likely to have severe pain which can be attributed to the treatment and associated with weight loss.

On the other hand, this condition may compromise the patient's ability to withstand the antineoplastic therapy, requiring radio and/or chemotherapy dose limitation, which may have an influence on an inappropriate therapy for cancer treatment.

For all this, it is desirable to provide new stable compositions useful for the treatment and prevention of mucositis, arid particularly oral mucositis caused by agents for cancer treatment. Likewise, it is required to provide new uses and methods for the treatment and prevention of oral mucositis associated, with cancer treatment.

PRIOR ART

A number of compounds for the prophylaxis and treatment of oral mucositis have been assessed in the prior art. Current therapies include cryotherapy to reduce pain and inflammation, analgesics to control pain, and antibiotics to control diseases caused by opportunistic bacteria. Analgesics, such as lidocaine-based mouthwashes are effective against pain for short periods of time but as time goes on, discomfort reappears.

Products for palliative care of oral mucositis known in the market are: Gelclair®, Mugard®, and Caphosol®; the use of other palifermin-based compositions (human keratinocyte growth factor, KGF); cytokines, and other inflammatory response modifiers such as IL-I, IL-II, TGF-beta-3; supplementation with amino acids, vitamins and laser therapy.

Document U.S. Pat. No. 6,509,028 discloses compositions comprising a mucoadhesive, a local anesthetic and an opioid (such as morphine or a pharmaceutically acceptable salt thereof). It is disclosed that these compositions are useful in topical administration, for example, as a liquid spray for the mouth mucous membrane or for the nasal cavity to induce mucosal anesthesia, for example, in cases of oral mucositis.

Chilean patent 44471 describes a formulation in the form of mouthwash and other useful forms for treating periodontal diseases and halitosis. It does not contain any ethanol, and claims the treatment of periodontal diseases in addition to preventing plaque formation, reducing caries formation, and inhibiting tartar formation.

Therefore, there exists the need to provide compositions and particularly new uses of said compositions in the treatment of oral mucositis and related symptoms, which are effective, stable, and with no undesirable side effects or intolerance.

SUMMARY OF THE INVENTION

If has been observed that an optimal solution for the success of therapy for mucositis is the use of a combination of treatment strategies focused on reducing inflammation, controlling bacteria, and decreasing pain.

The present invention combines the use of these three therapeutic effects, namely antimicrobial, anti-inflammatory, and the analgesic effect in one single pharmaceutical form.

The use of this pharmaceutical composition has shown, initially in the form of mouthwash, to be useful for the treatment and prevention of inflammatory, ulcerative and painful oral lesions of the oral mucosa and especially oral mucositis caused by chemotherapeutic and/or radiotherapeutic agents. Said composition comprises a series of components that confer an improved effect on compositions that are currently known in the prior art allowing effective prevention and improvement of the condition in a patient suffering from oral mucositis without unwanted side effects.

Preferably, the composition of the invention comprises one or more of the following components, in combination with pharmaceutically acceptable excipients or adjuvants; at least one antiseptic and/or antibacterial; at least one analgesic component; at least one anti-inflammatory, and optionally at least one plant extract, at least one sweetener, and one flavoring agent.

Particularly, the invention relates to the use of composition as defined herein in the treatment and/or prevention of oral mucositis, stomatitis and/or aphtous lesions particularly associated with anticancer therapies as well as to a method for the treatment or prevention of oral mucositis, stomatitis and/or aphthous lesions comprising applying to a patient a composition as described above.

DETAILED DESCRIPTION OF THE INVENTION

The invention relates to the use of a composition comprising the aforementioned active components, together with one or more pharmaceutically acceptable excipients.

The composition of the invention may be in any convenient physical form, but is preferably in the form of a fluid upon administration, such as a mouthwash.

Although mouthwash according to the invention comprises a number of components that are known in the art, it has not been disclosed in the prior art the use of a composition that combines the components described herein, with amounts being claimed later, and in a single composition, which has been proven to be effective in preventing, treating and curing symptoms associated with oral mucositis caused by antineoplastic treatments as demonstrated in the attached examples.

Preferably, the composition of the invention comprises one or more of the following components, in combination with pharmaceutically acceptable excipients or adjuvants; at least one antiseptic agent and/or one antibacterial agent; at least one essential oil; at least one phenolic antiseptic agent, at least one anti-inflammatory agent and, optionally, at least one plant extract, at least one sweetener, and a flavoring agent.

The composition components and proportions thereof of the invention are detailed below:

The composition of the invention comprises at least one antimicrobial or antiseptic substance, wherein said antimicrobial or antiseptic substance is a non-toxic substance for oral use.

As used herein, the term "an oral non-toxic and antiseptic substance" refers to an antiseptic agent which is safe (not resulting in unwanted side effects) at the recommended dosage when administered as instructed. For example, when used in a mouthwash, a non-toxic antiseptic agent should be nontoxic when rinsing the mouth with said mouthwash, and even if some of the agent as been swallowed.

There are a number of substances with antimicrobial or antiseptic properties, which are capable of destroying or preventing the growth of a pathogen. Examples of such antimicrobial or antiseptic substances or agents according to the invention include alcohol derivatives such as ethanol, isopropanol, derivatives of parabens, such as methylparaben, ethylparaben, butylparaben, propylparaben, peroxide derivatives such as hydrogen peroxide, carbamide peroxide as well as other antimicrobial or antiseptic agents such as chlorhexidine, chlorhexidine gluconate, cetylpyridinium chloride, triclosan, sodium hypochlorite, and the like.

According to the invention, the antimicrobial or antiseptic agent is selected from ethanol, which is incorporated in the compositions of the invention in amounts ranging from 0.001 to 0.08% w/w, and preferably in an amount of 0.02% w/w; isopropanol, which is added in amounts ranging from 0.001% to 0.5% w/w, and preferably in an amount of 0.1% w/w, methylparaben, ethylparaben, butylparaben, and propylparaben are added separately, in amounts ranging from 0.001% to 0.1% w/w and preferably in an amount of 0.06% w/w; hydrogen peroxide and/or the equivalent thereof in carbamide peroxide, which is added in an amount of 0.001% to 1% w/w, preferably in an amount between 0.01 and 0.1% and more preferably 0.05% w/w; chlorhexidine, which is added in an amount of 0.1 to 0.3% w/w, preferably in an amount of 0.11% w/w; cetylpyridinium chloride, which is added in an amount of 0.005% to 5% w/w, preferably in an amount of 0.02 to 2.5% w/w, and triclosan, which is added in an amount of 0.05% to 1% w/w, or mixtures thereof.

Other examples of antiseptic substances include a metal compound, a quaternary ammonium compound, iodine, or a phenolic compound. Examples of metal compounds that can be used according to the present invention include silver nitrate and silver sulfadiazine. Examples of quaternary ammonium compounds which can be used according to the present invention include diethyl benzyl ammonium chloride, didodecyl dimethyl ammonium chloride and benzalkonium chloride. Examples of phenolic compounds which may be used according to the invention include phenol, para-chlorometaxilenol, para-chlorophenol, cresol and hexylresorcinol.

Compounds silver nitrate and silver sulfadiazine are each added separately, in an amount of around 0.5 to 2% w/w, preferably in an amount of 1% w/w. Compounds diethyl benzyl ammonium chloride, dimethyl didodecyl ammonium chloride and benzalkonium chloride are each added separately in an amount of 0.1% to 2% w/w, preferably in an amount of 1% w/w. The phenol compounds, para-chlorometaxilenol, para-chlorophenol, cresol and hexylresorcinol are each added separately in an amount of 0.001% to 0.1% w/w, preferably in an amount of 0.003% to 0.08% w/w, and more preferably, in an amount of 0.004% w/w.

The composition of the invention may also comprise other agents that may provide benefits to the patient, such as antibiotics, zinc salts and/or fluoride derivatives. Additionally, the composition of the invention comprises at least one essential oil selected from thymol (also referred to as eucalyptol), menthol, eugenol, and methyl salicylate, which in addition to comprising antimicrobial properties; they provide analgesia and refreshing feeling to the patient.

Thymol, or else eucalyptol, is added in the compositions of the invention in amounts ranging from 0.001 to 0.08% w/w, and preferably in an amount of 0.02% w/w. Methyl salicylate is added in amounts ranging from 0.001% to 0.5% w/w, and preferably in an amount of 0.1% w/w. Menthol is added in amounts ranging from 0.001% to 0.1% w/w and preferably in an amount of 0.06% w/w. Eugenol is added in an amount from 0.005% to 0.04% w/w, and preferably in an amount of 0.008% to 0.03% w/w, and more preferably in an amount of 0.01% w/w.

The composition of the invention further comprises at least one natural anti-inflammatory agent, such as camphor. Said agent is added in amounts ranging from 0.006 to 0.05% w/w, preferably in amounts of between 0.009 and 0.02% w/w and more preferably in an amount of 0.012% w/w.

The composition of the invention optionally comprises at least one plant extract which is combined with other active ingredients to provide a synergistic effect in reducing or inhibiting bacterial growth on the surface of the oral mucosa, as well as to reduce inflammation of the mucosa caused by anticancer therapies.

According to a preferred embodiment of the invention, the plant extract is selected from chamomile extract, a plant species with antispasmodic, emollient, anti-inflammatory, astringent, antiseptic action, and a wound healing stimulator that promotes granulation and epithelization. The plant extract, is added in the compositions of the invention in amounts ranging from 0.05 to 0.5% w/w, and preferably in an amount of 0.1% w/w.

The composition of the invention further comprises flavoring agents which may be selected from any compound or mixture thereof that allows enhancement of the composition flavor. Suitable flavoring agents according to the invention are ingredients that provide fragrance and/or other sensory effect in the mouth, such as a refreshing or warm feeling. Such ingredients include, but are not limited to menthol, methyl acetate, methyl lactate, camphor, eucalyptus oil, eucalyptol, oxanone, orange essence, cherry essence, anise, papaya, among others. One or more flavoring agents are present in the composition of the invention in an amount from 0.01 to 5% w/w.

The composition of the invention further comprises pharmaceutically acceptable carriers or excipients. The one or more pharmaceutically acceptable carriers preferably contain a moisturizing agent to improve the feeling of the product in mouth and to prevent dehydration, as well as to solubilize certain active ingredients and to provide the composition with body and texture. Examples of moisturizing agents according to the invention include glycerin, sorbitol and glycols such as propylene glycol and polyethylene glycol and mixtures thereof. Glycerin is added in the compositions of the invention in amounts ranging from 0.05 to 0.5% w/w, and preferably in an amount of 0.1% w/w.

The composition of the invention further comprises sweetening agents. These sweetening agents for the use in oral compositions include for example, saccharin, dextrose, xylitol, sucrose, sucralose, stevia, and the like and are added in amounts of from 0.01 to 1.5% w/w.

The composition according to the invention is also useful in the preparation of a medicament for the treatment of aphthous lesions.

The composition according to the invention is also useful in the preparation of a medicament for the treatment of oral mucositis.

The pH of the oral compositions of the invention is within the range of 6.0 to 7.2, preferably from 6.5 to 7.2. Those skilled in the art may adjust the pH of the composition to the preferred ranges by adding an enough amount of a solution of sodium hydroxide, hydrochloric acid, phosphate buffer or buffers or other agent as appropriate, by means of methods which are known in the technique.

The compositions of the invention may be prepared by mixing each of the ingredients and adding them into an appropriate amount of water.

The skilled in the art will understand that the total of all ingredients (components) used in the composition of the invention sum up 100% by weight of the total composition. Furthermore, unless otherwise indicated, all percentages described herein are percentages by weight of the total composition.

The invention further provides the use of the composition in the treatment and/or prevention of oral mucositis or stomatitis.

The invention provides the use of the composition in the treatment and/or prevention of oral mucositis or stomatitis particularly associated with anticancer therapies comprising radiotherapy and/or chemotherapy.

Particularly, the invention relates to the use of any of the compositions described herein in the preparation of a medicament useful in the treatment and/or prevention of oral mucositis or stomatitis particularly associated with anticancer therapies comprising radiotherapy and/or chemotherapy.

Particularly, the invention provides the use of the composition described herein for the treatment of stomatitis.

Likewise, the invention provides a method for the treatment and/or prevention of oral mucositis or stomatitis particularly associated with anticancer therapies which comprise the steps of:

a. Provide an oral pharmaceutical composition comprising:
   i. at least one antiseptic agent selected from an alcohol derivative selected from ethanol, isopropanol, a paraben derivative selected from methyl paraben and ethyl paraben, butyl paraben, propylparaben, a derivative of peroxide selected from hydrogen peroxide, carbamide peroxide, and also selected from chlorhexidine, chlorhexidine gluconate, cetylpyridinium chloride, triclosan and sodium hypochlorite;

ii. an essential oil selected from thymol, menthol, eugenol and methyl salicylate
iii. a phenolic antiseptic agent selected from phenol, para-chloro-meta-xilenol, para-chlorophenol, cresol and hexylresorcinol;
iv. an agent with anti-inflammatory properties selected from camphor;
v. a flavoring agent selected from menthol, methyl acetate, methyl lactate, camphor, eucalyptus oil, eucalyptol, oxanone; and
vi. pharmaceutically acceptable excipients.

b. Apply the medicine in the oral cavity.

A method according to the invention comprises applying the composition at least three times a day, preferably at least 5 times a day, for at least 2 to 3 days, preferably at least 4 times a week.

The following examples are illustrative and should not be construed as limiting the invention in any circumstances. The skilled in the art will understand that it is possible to apply a number of variations to the invention which are within the spirit and scope of the appended claims.

EXAMPLE 1

Preparation of an Aqueous Solution for Mouthwash

| Ingredient | I % w/w | II) % w/w | III) % w/w | IV) % w/w |
|---|---|---|---|---|
| hydroxide peroxide | 0.12% | — | 0.05% | — |
| carbamide peroxide | — | — | — | 0.5% |
| cetylpiridynium chloride | — | 0.3% | — | — |
| parachlorophenol | 0.5% | 0.005% | 0.001% | — |
| eugenol | 0.03% | — | 0.01% | 0.03% |
| menthol | — | 0.06% | — | — |
| camphor | 0.013% | 0.01% | 0.01% | 0.01% |
| chamomile extract | 0.02% | — | 0.10% | — |
| xylitol | 5.00% | 5.00% | 5.00% | 5.00% |
| mint flavoring agent | 0.3% | 0.3% | 0.3% | 0.3% |
| sucralose | 0.02% | 0.02% | 0.02% | 0.02% |
| glycerine | 0.10% | 0.10% | 0.10% | 0.10% |
| demineralized water | csp 1000 g | csp 1000 g | csp 1000 g | csp 1000 g |

The composition is prepared as follows:
1. 800 ml of demineralized water are added into a beaker.
2. Subsequently, the components sucralose, camphor, hydrogen peroxide, parachlorophenol, glycerin, eugenol, chamomile extract, xylitol, blue dye and mint flavoring are added in the amounts described above.
3. Then, demineralized water is added to a total volume of 950 mL.
4. The pH is then adjusted to 7.00 using 0.1 N HCl or 0.1 N NaOH, or a suitable buffer such as beozoate/benzoic acid and complex to a weight of 1000 g with demineralised water.

EXAMPLE 2

Use of the Composition for the Treatment of Oral Mucositis in Patients Undergoing Chemotherapy During the second cycle of chemotherapy, a 40 years old woman, diagnosed with non-Hodgkin lymphoma, was receiving cancer treatment consisting of high-dose methotrexate and melphalan. During clinical assessment, a condition of oral mucositis grade 2 is diagnosed according to WHO scale (Table 1). The use of the oral rinse of the composition of Example 1 (III), 10 ml, 5 times a day, for 2 minutes is indicated.

Patient is monitored on the third day, showing complete remission of lesions and absence of inflammatory characteristics features or pain, reclassifying its initial mucositis to grade 0 according to WHO scale (Table 1).

This therapy is maintained throughout the cycle, not showing new oral lesions.

In a next cycle of chemotherapy, adriamycin, vincristine and cyclophosphamide was given, following with the mouthwash of the previous cycle, not showing oral lesions until the end of the therapy.

TABLE 1

WHO scale for the assessment of oral mucositis

| Scale | Description |
|---|---|
| 0 | No symptoms |
| 1 | Pain and erythema |
| 2 | Erythema, ulcers, ability to ingest a solid diet |
| 3 | Ulcers, extensive erythema, liquid diet is required |
| 4 | Unable to feed because of ulcers, intravenous feeding or tube feeding is required |

EXAMPLE 3

Use of the Composition for the Treatment of Oral Mucositis in Patient under Treatment with Concomitant Chemo-radiotherapy Male patient, diagnosed with tonsil cancer, prescribed with combined treatment of radiotherapy and chemotherapy (cispiatin).

On the fourth day of therapy, the patient develops oral mucositis grade 2 according to WHO scale (Table 1). Treatment was indicated with the composition of Example 1 (III), 10 ml for 2 minutes, 5 times a day. His oral condition is examined on the fourth day, showing complete remission of inflammation and absence of pain, mucositis being reclassified with value 0 in the WHO scale (Table 1).

EXAMPLE 4

Use of the Composition for the Treatment of Oral Mucositis in Patients with Radiotherapy Male patient, diagnosed with nasopharyngeal cancer. Radiotherapy treatment, 5,000 cGy per cycle, is started.

After a week of radiation therapy, the patient has painful ulcers and oral lesions that prevent him from feeding. Oral mucositis grade 3 is diagnosed according to WHO scale (Table 1) and supportive therapy is indicated with mouthwash of Example 1 (III), 10 ml, 5 times a day, for 2 minutes, showing remission of the lesions and pain after five days, his mouth state being reclassified as oral mucositis WHO grade zero (Table 1).

EXAMPLE 5

Use of the Composition for the Treatment of Recurrent Aphthous Stomatitis

Male patient, 40 years old. During oral exam, 4 painful and disabling ulcerative lesions are observed, 2 in the sublingual region and other 2 in the vestibular mucosa of the cheek, about 3 to 4 mm in size and whose diagnosis is recurrent aphthous stomatitis because the patient reports suffering from these lesions several times a year.

Total scaling therapy and prophylaxis is initiated, and daily use of the composition of Example 1 (III), 10 ml every 2 hours for 3 days is indicated.

On the first day, patient reported immediate pain relief and on the fourth day presents only traces of the initial painful ulcerative lesions. The patient fully recovered on the seventh day.

The invention claimed is:

1. A method for the treatment of mucositis or stomatitis, particularly associated with an anticancer therapy, comprising the steps of:
    a. providing an oral pharmaceutical composition in the form of an oral topical solution comprising:
        i. at least one antiseptic agent selected from the group consisting of:
            A) hydrogen peroxide and carbamide peroxide, and a mixture thereof, in an amount from 0.001% to 1% w/w composition,
            B) cetylpyridinium chloride, in an amount from 0.005% to 5% w/w composition, and
            C) a mixture thereof;
        ii. an essential oil consisting of eugenol, in an amount from 0.005% to 0.04% w/w composition;
        iii. a phenolic antiseptic agent consisting of para-chlorophenol, in an amount from 0.001% to 0.01% w/w composition;
        iv. an agent with anti-inflammatory properties consisting of camphor in an amount of from 0.006% to 0.05% w/w composition;
        v. a flavoring agent selected from the group consisting of menthol, methyl acetate, methyl lactate, camphor, eucalyptus oil, eucalyptol, and oxanone, and a mixture thereof, in an amount from 0.01% to 5% w/w composition;
        vi. a plant extract consisting of chamomile, in an amount from 0.05% to 0.5% w/w composition;
        vii. a sweetening agent selected from the group consisting of sucralose, xylitol and a mixture thereof in an amount of 0.01% to 15% w/w composition; and
        viii. a pharmaceutically acceptable excipient selected from the group consisting of glycerin, sorbitol and a glycol, in an amount from 0.05% to 0.5% w/w composition; and
    b. applying the oral pharmaceutical composition in the oral cavity of a patient having oral mucositis or stomatitis associated with an anticancer therapy, at least five times a day.

2. The method according to claim 1 wherein the oral mucositis is caused by an antineoplastic treatment, wherein the antineoplastic treatment is selected from the group consisting of chemotherapy and radiotherapy.

3. The method according to claim 2, wherein the chemotherapy employs a chemotherapy agent selected from the group consisting of melphalan, methotrexate, cisplatin, 5-fluorouracil, cyclophosphamide, fludarabine, adriamycin, vincristine sulfate, ifosfamide, etoposide, carmustine, cytarabine, and gemcitabine, and a mixture thereof.

4. The method according to claim 1, wherein the treatment comprises reducing inflammation and reducing pain caused by the oral mucositis or stomatitis.

* * * * *